United States Patent [19]

Mansfield et al.

[11] 4,026,665
[45] May 31, 1977

[54] METHOD AND APPARATUS FOR SULFUR ANALYSIS

[75] Inventors: Ernest Bryant Mansfield, Pittsburgh; Dennis A. Gibboney, Mount Pleasant, both of Pa.

[73] Assignee: Fisher Scientific Company, Pittsburgh, Pa.

[22] Filed: June 11, 1976

[21] Appl. No.: 695,207

[52] U.S. Cl. .................. 23/230 PC; 23/253 PC; 23/254 E; 23/255 E; 204/195 T
[51] Int. Cl.$^2$ .............. G01N 31/12; G01N 27/44; G01N 31/06; G01N 31/16
[58] Field of Search ..... 23/230 PC, 253 PC, 254 E, 23/232 E, 255 E; 204/195 T

[56] References Cited
UNITED STATES PATENTS

| | | | |
|---|---|---|---|
| 2,224,044 | 12/1940 | Francis | 23/230 PC |
| 2,754,178 | 7/1956 | Mack | 23/230 PC |
| 3,167,396 | 1/1965 | Staunton et al. | 23/253 PC |
| 3,529,937 | 9/1970 | Ihara et al. | 23/253 PC |
| 3,650,696 | 3/1972 | Eads | 23/230 PC |
| R24,553 | 10/1958 | Krasl et al. | 23/253 PC |

Primary Examiner—R.E. Serwin
Attorney, Agent, or Firm—Webb, Burden, Robinson & Webb

[57] ABSTRACT

Our system for determining the sulfur content of a sample includes combusting the sample to form a gas in which the sulfur is converted primarily to sulfur dioxide in known ratio with the sulfur trioxide. The gas sample is passed into a reaction vessel containing a substantially pyridine solvent. The sulfur dioxide is scrubbed from the sample (trapping) via a binding action with the pyridine. The bound sulfur dioxide is titrated with elemental iodine in the presence of alcohol and excess water. The trapping and titration sequence can be simultaneous and continuous. A polarized electrode pair is preferably employed as the detection means with the end point determination occurring when the electrodes become current conducting in the presence of excess iodine. The titrant volume is then converted to a sulfur analysis by standard means. The apparatus is disclosed for carrying out the method.

15 Claims, 2 Drawing Figures

METHOD AND APPARATUS FOR SULFUR ANALYSIS

FIELD OF THE INVENTION

Our method and apparatus is directed to sulfur determination and, more particularly, to sulfur determination from a sample in which the sulfur has been combusted to primarily sulfur dioxide in the gaseous state.

DESCRIPTION OF THE PRIOR ART

Sulfur analysis in many industries has become extremely important with the advent of increasingly stringent anti-pollution government requirements. The sulfur content of coal, iron ore, glass, wood, oil, chemicals and many other products has become a recognized indicator of the potential pollution emission of these industries.

The difficulty in obtaining reproducible sulfur analysis results is exemplified by coal, which is an exceedingly complex and varied material susceptible to wide chemical variation due to such factors as the intrusion of mineral strata. These characteristics lead to sulfur analysis difficulties which must be resolved before reproducible sulfur analysis can be relied upon. Sulfur in coal will normally be in a number of forms which may include organic, free, inorganic sulfides, low stability sulfates and highly stable sulfates. Of these sulfur forms, the first four represent available sulfur in the sense that they decompose during coal combustion to produce gaseous sulfur oxides which contribute to air pollution. The highly stable sulfates cannot be decomposed by temperatures in standard combustion processes and, therefore, are not air pollution factors which need be taken into account.

Present methods for analyzing sulfur include a "referee" method which is a laborious wet oxidation procedure which measures the total sulfur. Of course, measuring total sulfur where only available sulfur is of concern, has led to confusion. Substantial variations between the total sulfur method and the combustion available sulfur methods arise when specific coals are tested which have, for example, high levels of gypsum or limestone.

As a result of these problems, coal labs have historically tested by known combustion methods which do not give good reproducibility and then applied an arithmetic factor to conform with total sulfur data. All of these problems could be alleviated with a rapid, reproducible sulfur analyzing method. Previous combustion methods have led to low efficiencies as a result of utilizing water based scrubbing solvents which do not achieve reproducible removal of the sulfur and in which the results are easily interfered with by other constituents in the sample such as chloride.

SUMMARY OF THE INVENTION

Our invention provides a sulfur analyzing system in which the results are easily obtained and reproducible with a high degree of accuracy. The sulfur in the form of sulfur dioxide is efficiently and totally removed from the gas sample. The system is amenable to total automation so that the sulfur sample goes in the furnace and the digital readout of sulfur follows shortly thereafter. Further, the titrant can be recycled many times, thereby diminishing the cost of running the test.

Our sulfur analyzing system involves a sample, e.g., coal, combustion to convert the sulfur to sulfur dioxide followed by the amperometric titration of the sulfur dioxide with iodine. The sulfur dioxide is scrubbed from the sample through the use of a pyridine solvent which is essentially 100% efficient as the result of the sulfur dioxide being a strong Lewis acid and the pyridine being a strong Lewis base. The solution containing the sulfur dioxide bound to the pyridine is titrated with iodine in an excess water environment and in the presence of a polarized electrode pair which becomes current conducting in the presence of an excess of iodine. The titrant volume is automatically converted to a sulfur analysis.

DESCRIPTION OF THE PREFERRED EMBODIMENTS

Figure 1:
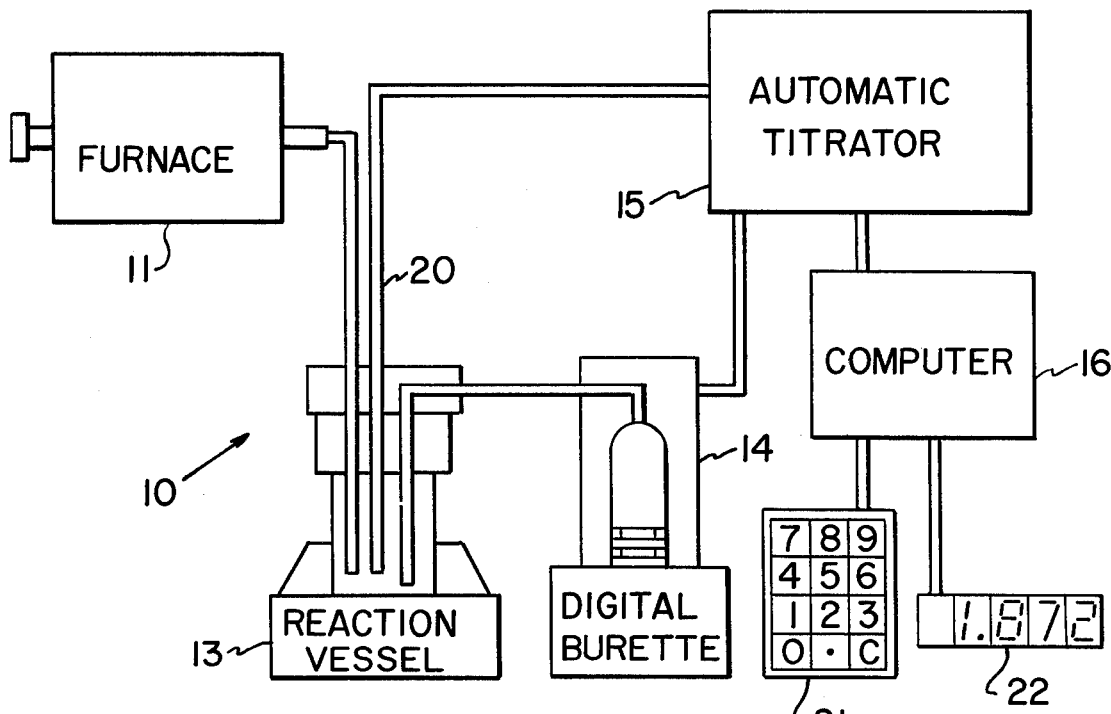
FIG. 1 is a block schematic of our sulfur analyzer system.

The instrumentation for the sulfur analyzer, generally designated 10, comprises six basic components. These components are a sample combustion furnace 11, a gas scrubber-titration reaction vessel 13, a titrant demand circuitry in the form of an automatic titrator 15, a digital burette 14, a detection device in the form of an electrode pair 20 and a computer digital display module 16 having an input keyboard 21 and a readout display 22, FIG. 1.

The combustion furnace 11 combusts the sulfur bearing sample, generally 0.1 to 2 gr., in a combustion boat, in the presence of oxygen (from an oxygen tank) and a suitable catalyst in accordance with the following combustion reaction.

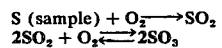

By maintaining proper combustion conditions in regard to temperature, the furnace produces a sulfur dioxide-sulfur trioxide equilibrium that strongly favors the production of sulfur dioxide. Such equilibrium factors are generally known. The utilization of a catalyst such as platinized asbestos or vanadium pentoxide enhances the rate at which the equilibrium between the sulfur dioxide and sulfur trioxide is achieved. The equilibrium constant is a strong function of temperature with a temperature of at least 1350° C producing an acceptably small amount of sulfur trioxide. Consistent results have also been achieved at higher temperatures such as 1500° C but no diminution of sulfur recovery or precision of results were observed at the lower combustion temperature. Standard curves are available which give the per cent of sulfur trioxide in equilibrium mixtures of sulfur dioxide at unit oxygen activity as a function of temperature. Using oxygen as a carrier gas for the sample minimizes a carbon build-up in the tubing.

In order to affect the analysis, the sulfur dioxide must be scrubbed out of the combustion gas sample and collected in a liquid reaction vessel for analysis. The success of the analysis is totally dependent upon the scrubbing efficiency since any escaping sulfur dioxide is lost for the analysis. Scrubbing in our system is conducted by passing the gas sample into reaction vessel 13 which contains substantial amounts of a pyridine solvent. Pyridine, which is a strong Lewis base, strongly binds sulfur dioxide which is a strong Lewis acid in accordance with the following reaction.

$$C_5H_5N: + SO_2 \longrightarrow C_5H_5N:SO_2$$

A scrubbing solution containing roughly 30% pyridine in methyl alcohol and water gives strongly reproducible and linear analytical results, even without the use of sophisticated scrubbing apparatus. Sulfur dioxide gas injected below the surface of such a solution is observed to immediately dissolve with no bubbles reaching the surface under reasonable flow rates. Stirring by a bar magnet is normally provided in the reaction vessel 13. A standard vacuum system is utilized to provide inflow of the sample gas into the reaction vessel and to exhaust gases from the system. The vacuum source also serves to pump excess liquid from the reaction vessel.

While the sulfur dioxide is scrubbed from the gas sample and bound to the pyridine, the titration takes place. Although the trapping and titration sequences can be separate, we have found consistent and stable results with a continuous titration. The titration performed is somewhat similar to the Karl Fisher titration method for water. In the standard Karl Fisher method, a titrant of iodine in excess sulfur dioxide, pyridine and alcohol is used to titrate water from a sample such as oil. In the subject application the titration is to analyze for sulfur dioxide and, therefore, a substantial molar excess of water instead of sulfur dioxide is provided. The sulfur dioxide as the analyzate and the iodine as a titrant then become the limiting reagents in the analysis.

The titrant is actually a combination of iodine, pyridine, methyl alcohol and water. The titrant reacts with the scrubbed sulfur dioxide in the following two step reaction.

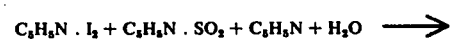

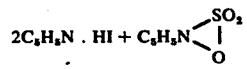

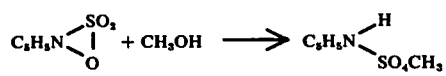

The scrubbing (trapping) and titration can be done continuously rather than separately and still produce consistent and stable results. A typical titrant-scrubbing solution will have the following composition: 700 ml. methyl alcohol, 280 ml. pyridine, 20 ml. water and approximately 4 gr. of iodine. The titrant once used can be recycled many times by merely replenishing the iodine.

Two difficulties, common to the standard Karl Fisher titrant, do not occur in the subject titration. The Karl Fisher titrant is inherently unstable since its titer changes by picking up atmospheric moisture and volatilizing the iodine. The subject titrant is unaffected by moisture (it already has a molar excess of water) and shows little tendency to volatilize iodine at atmospheric pressure. Further, the vapor pressure of iodine in pyridine in the absence of sulfur dioxide (as in the subject invention) is nearly negligible. Further, the titrant possesses the unusual property of being recyclable.

The titration is done by an automatic titrator 15 which controls the digital burette 14 which provides the titrant to the reaction vessel 13. When the automatic titrator detects the end point, it automatically closes off the titrant flow. The detection system preferably consists of a pair of inert electrodes, shown schematically as 20, such as platinum placed in series with a microammeter. A small constant voltage is placed across the electrodes. The voltage produces minimal current since the scrubbing solution itself, and even with sulfur dioxide present, is substantially nonconductive. As the iodine titrant is added to the solution by the automatic titrator and through the digital burette, the sulfur dioxide present progressively reacts with the iodine-pyridine complex. At the time when all the sulfur dioxide has been destroyed and titrant addition is momentarily continued, the excess iodine-pyridine complex forms. This complex is highly conductive and depolarizes the electrodes with the production of a large, observable current on the microammeter.

The amount of sulfur dioxide produced by the sample is then related to the titrant volume required in an apparatus such as the Titralyzer Concentration Computer manufactured by the assignee of the subject invention.

The per cent sulfur is readily determined in accordance with the following formula:

$$\%S = \frac{(\alpha - \beta) \cdot \gamma \cdot \sigma}{\Delta}$$

where
$\alpha$ = titrant vol. (ml.)
$\delta$ = blank volume in burette
$\gamma$ = titrant equivalence (mg. S)/ml.
$\Delta$ = sample wt. (mg.)
$\delta$ = 100% ($10^6$ for ppm S)

The sample weight is merely entered into the input board 21 and the % sulfur (or ppm) is displayed on the readout 22.

Figure 2:
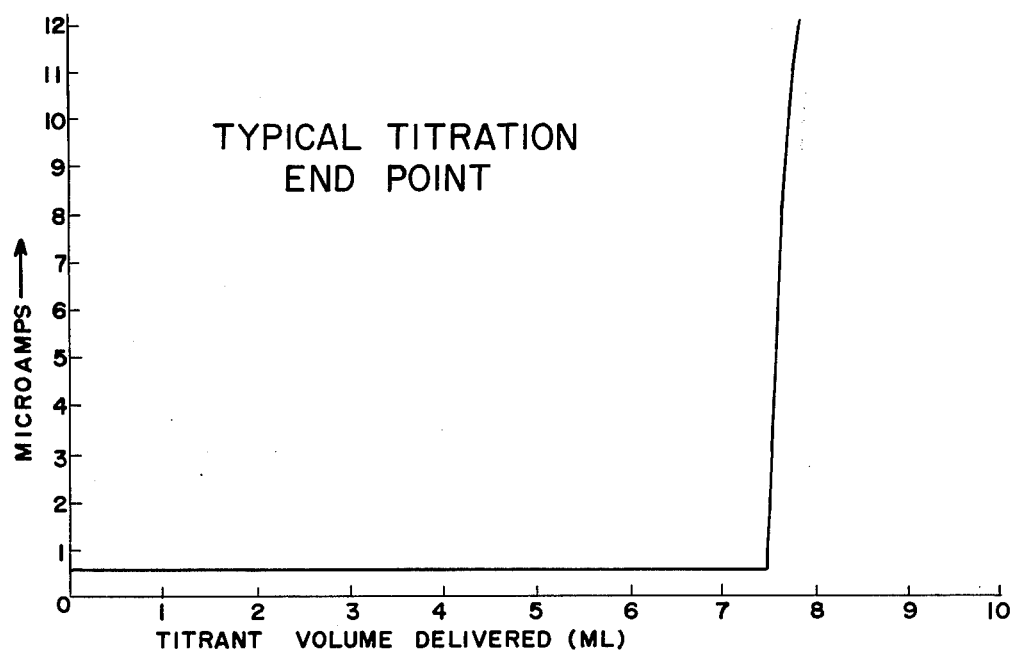
FIG. 2 is a graph showing an end point determination for the titration.

The end point of the reaction is very abrupt as shown in FIG. 2 wherein microamps are plotted against the titrant volume delivered in milliliters. This very strong and detectable end point is illustrated for a typical titration made in accordance with the subject invention.

Chloride is a known element in coal which causes interference with existing sulfur analyzers. Analyses made in accordance with the subject invention were made with intentional additions of varying percentages of chlorine added. It was found that at chlorine concentrations representative of real coals, the relative error is less than ½ per cent and thus is negligible for normal sulfur analysis requirements.

We claim:
1. A method for determining the sulfur content of a sample comprising:
A. combusting a sulfur-bearing sample to form a gas sample in which the sulfur is substantially in the form of sulfur dioxide;
B. treating the gas sample with a Lewis base solvent to scrub out the sulfur dioxide by binding it to the Lewis base;
C. titrating the bound sulfur dioxide with a titrant;
D. detecting the end point of the titration and the titrant volume employed; and
E. converting the titrant volume to the amount of sulfur in the sample.
2. The method of claim 1 wherein the Lewis base is pyridine.

3. The method of claim 1 wherein the titrant is iodine.

4. The method of claim 3 wherein the iodine titrant comprises iodine, pyridine, methyl alcohol and water.

5. The method of claim 2 wherein the pyridine solvent includes at least 30% pyridine, the balance being a molar excess of water and alcohol.

6. The method of claim 2 wherein the treating step includes passing the gas sample into a reaction vessel containing the solvent.

7. The method of claim 2 wherein the treating step includes stirring the gas sample and pyridine solvent in the reaction vessel.

8. The method of claim 2 wherein the detecting step includes subjecting the bound sulfur dioxide and iodine titrant to polarized electrodes during titration which become current conducting at the end point.

9. The method of claim 2 including recycling the iodine titrant by replacing spent iodine.

10. The method of claim 2 including combining the treating step B) and the titrating step C) into a single, continuous and simultaneous treating and titrating.

11. In a method for determining sulfur content by combusting a sulfur-bearing sample into a gas sample containing sulfur in the form of primarily sulfur dioxide of known ratio with sulfur trioxide, the improvement comprising separating the sulfur dioxide from the gas sample by scrubbing it with a pyridine solvent to bind the sulfur dioxide to the pyridine.

12. The method of claim 11, said scrubbing solvent comprising at least 30% pyridine, the balance being a molar excess of water and alcohol.

13. A method for determining the sulfur content of a sample comprising:
   A. combusting the sample to form a gas sample in which the sulfur is primarily sulfur dioxide in known ratio with sulfur trioxide;
   B. passing the gas sample into a reaction vessel containing a pyridine solvent of at least 30% pyridine;
   C. separating the sulfur dioxide from the gas sample by binding it to the pyridine;
   D. titrating the separated sulfur dioxide with an elemental iodine based titrant including pyridine, methyl alcohol and water in the presence of a polarized electrode pair;
   E. measuring the titrant volume at an end point of the titration, said end point being amperometrically determined when the electrodes become current conducting in the presence of excess iodine; and
   F. converting the titrant volume to a sulfur analysis.

14. The method of claim 13 wherein the sample is combusted at about 1350° C.

15. The method of claim 13 including using oxygen as a carrier gas for passing the gas sample into the reaction vessel.

* * * * *